(12) United States Patent
Wang et al.

(10) Patent No.: US 9,335,285 B2
(45) Date of Patent: May 10, 2016

(54) METHOD FOR MEASURING ACID STRENGTH IN REACTION MEDIUM USING TRIMETHYLPHOSPHINE OXIDE AND $^{31}$P NMR

(71) Applicant: ExxonMobil Chemical Patents Inc., Baytown, TX (US)

(72) Inventors: Kun Wang, Bridgewater, NJ (US); Roberto Garcia, Easton, PA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 119 days.

(21) Appl. No.: 14/498,332

(22) Filed: Sep. 26, 2014

(65) Prior Publication Data

US 2015/0111302 A1    Apr. 23, 2015

Related U.S. Application Data

(60) Provisional application No. 61/892,712, filed on Oct. 18, 2013.

(30) Foreign Application Priority Data

Jan. 21, 2014  (EP) .................................... 14151874

(51) Int. Cl.
*G01N 31/22* (2006.01)
*G01N 24/08* (2006.01)
(Continued)

(52) U.S. Cl.
CPC .............. *G01N 24/088* (2013.01); *C07C 37/08* (2013.01); *C07C 45/53* (2013.01); *G01N 24/085* (2013.01); *G01N 31/221* (2013.01); *G01R 33/46* (2013.01);
(Continued)

(58) Field of Classification Search
CPC ... G01N 31/22; G01N 24/088; G01N 24/085; G01N 31/221
USPC ............................ 436/61, 100, 102, 163, 173
See application file for complete search history.

(56) References Cited

U.S. PATENT DOCUMENTS 4,439,409 A    3/1984  Puppe et al.
4,826,667 A    5/1989  Zones et al.
(Continued)

FOREIGN PATENT DOCUMENTS

EP         0293032      11/1988
WO      WO 97/17290      5/1997
(Continued)

OTHER PUBLICATIONS

Verkade, J. G. et al, Inorganic Chemistry 1964, 3, 884-889.*
(Continued)

*Primary Examiner* — Arlen Soderquist
(74) *Attorney, Agent, or Firm* — Siwen Chen

(57) ABSTRACT

A method to determine the strength of an acid in a medium is disclosed. The method includes (I) providing multiple samples comprising trimethylphosphine oxide (TMPO), the acid, and the medium, wherein the multiple samples have different [H$^+$]/[TMPO] ratios, [H$^+$] is the concentration of hydrons in the sample in mole·liter$^{-1}$, and [TMPO] is the concentration of TMPO in the sample in mole·liter$^{-1}$. (II) The $^{31}$P chemical shifts of the multiple samples are measured by $^{31}$P NMR and compared to standardized samples to determine the acid strength of the medium.

21 Claims, 3 Drawing Sheets

(51) Int. Cl.
*C07C 37/08* (2006.01)
*G01R 33/46* (2006.01)
*C07C 45/53* (2006.01)

(52) U.S. Cl.
CPC ... *C07C 2101/14* (2013.01); *Y10T 436/163333* (2015.01)

(56) References Cited

U.S. PATENT DOCUMENTS

| | | | |
|---|---|---|---|
| 4,954,325 A | 9/1990 | Rubin et al. | |
| 5,066,373 A | 11/1991 | Levy et al. | |
| 5,236,575 A | 8/1993 | Bennett et al. | |
| 5,250,277 A | 10/1993 | Kresge et al. | |
| 5,362,697 A | 11/1994 | Fung et al. | |
| 5,831,139 A * | 11/1998 | Schmidt | C10G 59/00 585/310 |
| 6,037,513 A | 3/2000 | Chang et al. | |
| 6,049,018 A | 4/2000 | Calabro et al. | |
| 6,077,498 A | 6/2000 | Diaz Cabañas et al. | |
| 6,528,656 B1 * | 3/2003 | Pietri | C07F 9/5726 436/163 |
| 6,720,462 B2 | 4/2004 | Kuhnle et al. | |
| 6,730,625 B1 | 5/2004 | Chang et al. | |
| 6,756,030 B1 | 6/2004 | Rohde et al. | |
| 7,579,511 B1 | 8/2009 | Dakka et al. | |
| 2003/0186444 A1 * | 10/2003 | White | G01N 24/08 436/37 |
| 2005/0101814 A1 * | 5/2005 | Foley | C10G 45/62 585/317 |

FOREIGN PATENT DOCUMENTS

| | | |
|---|---|---|
| WO | WO 2009/128984 | 10/2009 |
| WO | WO 2009/131769 | 10/2009 |
| WO | WO 2012/036822 | 3/2012 |

OTHER PUBLICATIONS

Riddle, F. J. Jr., Journal of the American Chemical Society 1990, 112, 3259-3264.*
Rakiewicz, E. F. et al, Journal of Physical CHemistry B 1998, 102, 2890-2896.*
Brabston, D., "On-Line Analytical Options for Acid Monitoring" 1999, 23 pages downloaded from http://www2.dupont.com/Clean_Technologies/en_US/assets/downloads/AnalyticalOptionsforOnline.pdf.*
Nakajima, K. et al, Journal of the American Ceramic Society 2007, 90, 3725-3734.*
Brunner, E. et al, Molecular Sieves 2008, 6, 1-43.*
Sadakane et al., "*Thermal Stability and Acidic Strength of Preyssler-Type Phosphotungstic Acid, $H_{14}[P_5W_{30}O_{110}Na]$ and It's Catalytic Activity for Hydrolysis of Alkyl Acetates*," Z. Anorg. Allg. Chem. 2011, 637, (14-15), pp. 2120-2124.
Gordon et al., "*The Chemist's Companion: A Handbook of Practical Data, Techniques, and References*", Wiley, 1972, pp. 293-296.
U.S. Appl. No. 61/885,336, entitled, "*Hydroalkylating Process*", filed Oct. 1, 2013.
U.S. Appl. No. 61/729,019, entitled, "*Process for Producing Phenol*", filed Nov. 21, 2012.
U.S. Appl. No. 61/841,072, entitled "*Process for Concentrating a Mixture Containing Organic Hydroperoxide*", filed Jun. 28, 2013.
Zhao et al., "*Discernment and Quantification of Internal and External Acid Sites on Zeolites*", The Journal of Physical Chemistry B, 2002, vol. 106, Issue 17, pp. 4462-4469.

* cited by examiner

METHOD FOR MEASURING ACID STRENGTH IN REACTION MEDIUM USING TRIMETHYLPHOSPHINE OXIDE AND $^{31}$P NMR

PRIORITY CLAIM

This application claims priority to U.S. Provisional Application Ser. No. 61/892,712 filed Oct. 18, 2013, and European Application No. 14151874.6 filed Jan. 21, 2014, the disclosures of which are fully incorporated herein by their reference.

FIELD

The present disclosure relates to a high-sensitivity method to measure acid strength in a reaction mixture, and using such method for monitoring acid catalyzed processes for producing products such as phenol.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process via cumene. This is a three-step process in which the first step involves alkylation of benzene with propylene in the presence of an acidic catalyst to produce cumene. The second step is oxidation, preferably aerobic oxidation, of the cumene to the corresponding cumene hydroperoxide. The third step is the cleavage of the cumene hydroperoxide in the presence of heterogeneous or homogeneous catalysts into equimolar amounts of phenol and acetone, a co-product. However, the world demand for phenol is growing more rapidly than that for the acetone co-product. In addition, due to developing shortages in supply, the cost of propylene is likely to increase.

Alternatively, phenol and cyclohexanone can be co-produced by a variation of the Hock process in which cyclohexylbenzene is oxidized to obtain cyclohexylbenzene hydroperoxide and the hydroperoxide is decomposed in the presence of an acid catalyst to the desired phenol and cyclohexanone. Although various methods are available for the production of cyclohexylbenzene, a preferred route is disclosed in U.S. Pat. No. 6,037,513, which discloses that cyclohexylbenzene can be produced by contacting benzene with hydrogen in the presence of a bifunctional catalyst comprising a molecular sieve of the MCM-22 family and at least one hydrogenation metal selected from palladium, ruthenium, nickel, cobalt, and mixtures thereof. This reference patent also discloses that the resultant cyclohexylbenzene can be oxidized to the corresponding hydroperoxide which is then decomposed to the desired phenol and cyclohexanone co-product.

Although the production of phenol and cyclohexanone from cyclohexylbenzene appears to be analogous to the Hock process for producing phenol and acetone from cumene, the chemistries in each step are actually very different. For example, the chemistry of the cleavage of cyclohexylbenzene hydroperoxide is much more complicated than that for cumene hydroperoxide and more by-products (both in types and amounts) can form. Thus, cleavage of cyclohexylbenzene hydroperoxide to phenol and cyclohexanone is acid catalyzed and, although a variety of acid catalysts can be used, sulfuric acid is preferred for its low cost and easy availability. However, significant yield loss to by-product (both primary and secondary) can occur in the sulfuric acid-based cleavage of cyclohexylbenzene hydroperoxide if the acid strength in the reaction medium is not appropriate. Primary by-products may include the β-scission products such as hexanophenone and 6-hydroxylhexanophenone (6-HHP). Examples of secondary by-products include those derived from cyclohexanone, such as 2-(1-cyclohexenyl)cylohexanone and 2-(cyclohexylidene)cyclohexanone (cyclohexanone aldol condensation products), 2-hydroxycyclohexanone and cyclohexenone (cyclohexanone oxidation products). Formation of the primary by-products result in loss of both phenol and cyclohexanone; while secondary by-products further reduce yield to cyclohexanone.

The ability to monitor and adjust acid strength in the cleavage medium is desired. However, there is no method to measure the acid strength in the cleavage medium. Conventional methods to measure acid strength in solution include pH measurement (for aqueous solutions) and ion conductivity measurement. However, these methods are not sensitive enough for the low acid concentrations (e.g., up to thousands of ppm) used in cleavage process and are not sensitive enough to determine the difference among a wide range of solution compositions.

Therefore, a need exists for a detection method that addresses one or more of the above identified issues.

SUMMARY

The present disclosure provides a high-sensitivity method for accurately determining the strength of an acid in a reaction medium.

A process for co-production of phenol and cyclohexanone via cyclohexylbenzene (CHB) oxidation is disclosed herein that the cleavage step can be monitored via the strength of acid in the reaction medium. Sulfuric acid is used for cyclohexylbenzene hydroperoxide (CHBHP) cleavage in the process. It has been found that the composition of the cleavage medium is critical to achieving high yield of the conversion of cyclohexylbenzene to phenol and cyclohexanone: the higher the phenol content, the better the cleavage. This observation led to the implementation of concentrating the CHBHP cleavage feed and/or recycling the phenol/cyclohexanone azeotrope to the cleavage reaction. The amount of water can also affect the cleavage rate and yield. It was determined that with an appropriate cleavage medium, the sulfuric acid strength is highest and the primary cleavage reaction is significantly enhanced, thus improving the yield.

Prior to the present disclosure, a method to measure and/or determine sulfuric acid strength in a cleavage medium was not available. Conventional methods such as pH and ionic conductivity measurements are not sensitive for the low acid concentrations (e.g., up to thousands of ppm) used in the cleavage reaction. Therefore, it is desirable to have a reliable and easy-to-use method to measure the acid strength, which can be used to guide the operation and optimization of the cleavage step to produce, for example, phenol and cyclohexanone.

Accordingly, a first aspect of the present disclosure relates to a method to determine the strength of an acid in a medium comprising:

(I) providing multiple samples comprising trimethylphosphine oxide (TMPO), the acid, and the medium, the multiple samples having different [H$^+$]/[TMPO] ratios of less than 1.0, where [H$^+$] is the concentration of hydrons in the sample in mole·liter$^{-1}$, and [TMPO] is the concentration of TMPO in the sample in mole·liter$^{-1}$;

(II) measuring the $^{31}$P chemical shifts of the multiple samples by $^{31}$P NMR; and (III) plotting the chemical shifts against the [H$^+$]/[TMPO] ratios to determine the slope of the linear fit.

A second aspect of the present disclosure relates to method for optimizing reaction conditions of a reaction system, the method comprising:

(A) providing a sample comprising a reaction medium and an acid;

(B) combining trimethylphosphine oxide (TMPO) with aliquots of the sample to provide a series of mixtures containing both TMPO and protonated TMPO and having different [H$^+$]/[TMPO] ratios of less than 1.0;

(C) measuring the chemical shifts of the mixtures by $^{31}$P NMR;

(D) plotting the chemical shifts against the [H$^+$]/[TMPO] ratios to determine the slope of a linear fit;

(E) comparing the slope of the linear fit to that of a standardized sample comprising the same components of the reaction medium; and (F) determining whether one or more components of the reaction medium and/or amount thereof should be adjusted to provide for a desired acid strength.

A third aspect of the present disclosure relates to a method for monitoring a process for producing phenol and cyclohexanone, the process comprising:

(a) providing a cleavage feed containing greater than 10 wt % and no greater than 95 wt % cyclohexyl-1-phenyl-1-hydroperoxide, and at least 5 wt % and less than 90 wt % cyclohexylbenzene;

(b) mixing the cleavage feed with at least phenol, cyclohexanone, water, and sulfuric acid, to produce a cleavage reaction mixture containing from 10 wt % to 80 wt % phenol, from 10 wt % to 60 wt % cyclohexanone, from 0.5 wt % to 10 wt % cyclohexyl-1-phenyl-1-hydroperoxide, from 3 wt % to 60 wt % cyclohexylbenzene, from 0.01 wt % to 4 wt % water, and from 10 ppm to 1000 ppm sulfuric acid, where all concentrations are based on the total weight of the cleavage reaction mixture; and (c) reacting the cleavage reaction mixture at a temperature from 20° C. and to 90° C. for a time sufficient to convert at least 50% of the cyclohexyl-1-phenyl-1-hydroperoxide in the cleavage reaction mixture and produce a cleavage effluent containing phenol and cyclohexanone; wherein the process is monitored by:

(m1) taking a sample of the cleavage reaction mixture;

(m2) combining trimethylphosphine oxide (TMPO) with a series of aliquots of the sample to provide a series of mixtures containing both TMPO and protonated TMPO and having different [H$^+$]/[TMPO] ratios of less than 1.0;

(m3) measuring the chemical shifts of the mixtures by $^{31}$P NMR;

(m4) plotting the chemical shifts against the [H$^+$]/[TMPO] ratios to determine the slope of the linear fit;

(m5) comparing the slope of the linear fit to that of a standardized sample comprising the same components of the reaction medium; and (m6) determining whether one or more components of the cleavage mixture and/or amount thereof should be adjusted to provide for a desired acid strength.

A fourth aspect of the present disclosure relates to a method to monitor a process for a process for producing phenol and cyclohexanone, the process comprising:

(a) providing a cleavage feed containing cyclohexyl-1-phenyl-1-hydroperoxide;

(b) mixing the cleavage feed with at least phenol and cyclohexanone to produce a cleavage reaction mixture; and (c) reacting the cleavage reaction mixture in the presence of a sulfuric acid catalyst under conditions to maintain the weight ratio of phenol to cyclohexanone in the cleavage reaction mixture in excess of 1:1 and to convert part of the cyclohexyl-1-phenyl-1-hydroperoxide in the cleavage reaction mixture and produce a cleavage effluent containing phenol and cyclohexanone, wherein the process is monitored by removing a sample of the cleavage reaction medium having sulfuric acid present comprising the steps;

(d) combining trimethylphosphine oxide (TMPO) with the sample to provide a series of mixtures having different [H$^+$]/[TMPO] ratios of less than 1.0 and containing both TMPO and protonated TMPO;

(e) measuring the chemical shift of mixtures by $^{31}$P NMR;

(f) plotting the chemical shifts against the [H$^+$]/[TMPO] ratios to determine the slope of the linear fit;

(g) comparing the slope of the linear fit to that of a standardized sample comprising the same components of the reaction medium; and (h) determining whether one or more components of the reaction medium should be adjusted to provide for maximum acid strength.

DETAILED DESCRIPTION OF THE DISCLOSURE

Figure 1:
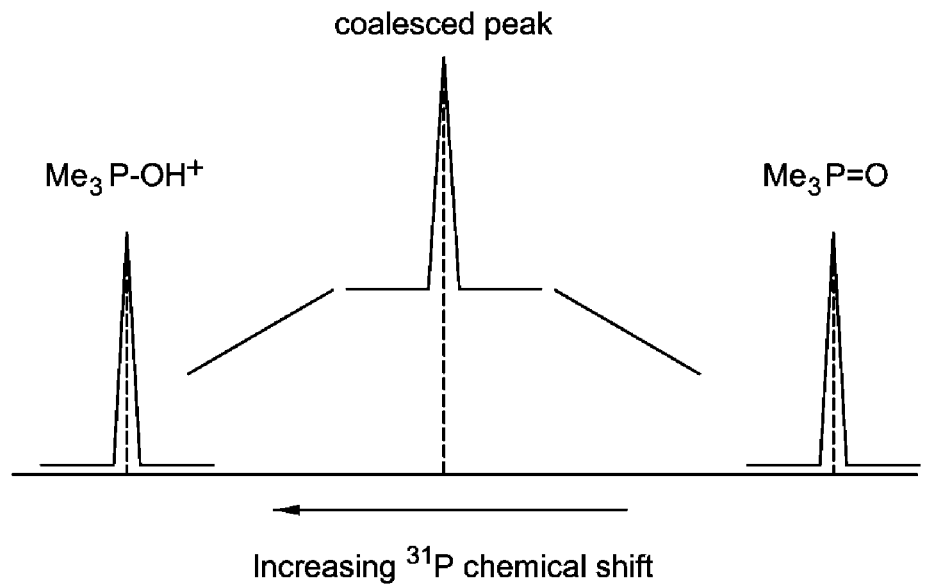
FIG. 1 is a diagram illustrating a $^{31}$P NMR coalesced peak from the reaction mixture of TMPO with H$^+$ resulting in equilibrium between TMPO, H$^+$ and TMPOH$^+$.

In the present disclosure, a process is described as comprising at least one "step". It should be understood that each step is an action or operation that may be conducted once or multiple times in the process, in a continuous or discontinuous fashion. Unless specified to the contrary or the context clearly indicates otherwise, the steps in a process may be conducted sequentially in the order as they are listed, with or without overlapping with one or more other step(s), or in any other order, as the case may be. In addition, two or more or even all steps may be conducted simultaneously with regard to the same or different batch of material. For example, in a continuous process, while a first step in a process is being conducted with respect to a raw material just fed into the beginning of the process, a second step may be conducted simultaneously with respect to an intermediate material resulting from treating the raw materials fed into the process at an earlier time in the first step. Preferably, however, steps are performed in the order listed.

Unless otherwise indicated, all numbers indicating quantities in the present disclosure are to be understood as being modified by the term "about" in all instances. It should also be understood that the precise numerical values used in the specification and claims constitute specific aspects disclosed herein. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, using "a hydrogenating metal" include where one, two or more hydrogenating metals are used, unless specified to the contrary or the context clearly indicates that only one hydrogenating metal is used. Likewise, "an oxygenated hydrocarbon" should be interpreted to include one or more types of hydrogenated hydrocarbon at various concentrations unless specified or indicated by the context to mean only one specific type of hydrogenated hydrocarbon.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question unless specified or indicated otherwise. All ranges expressed herein should include both end points as two specific aspects unless specified or indicated to the contrary.

As used herein, the generic term "phenylcyclohexene" includes, in the aggregate, 2-phenyl-1-cyclohexene, 3-phenyl-1-cyclohexene, and 4-phenyl-1-cyclohexene, unless clearly specified to mean only one or two thereof.

The term "MCM-22 type material" (or "material of the MCM-22 type," "molecular sieve of the MCM-22 type," or "MCM-22 type zeolite"), as used herein, includes one or more of:

molecular sieves made from a common first degree crystalline building block unit cell, which unit cell has the MWW framework topology. A unit cell is a spatial arrangement of atoms which if tiled in three-dimensional space describes the crystal structure. Such crystal structures are discussed in the "Atlas of Zeolite Framework Types," Fifth Edition, 2001, the entire content of which is incorporated as reference;

molecular sieves made from a common second degree building block, being a 2-dimensional tiling of such MWW framework topology unit cells, forming a monolayer of one unit cell thickness, desirably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 type include those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Materials of the MCM-22 type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Other molecular sieves, such as UZM-8 (described in U.S. Pat. No. 6,756,030), may be used alone or together with the MCM-22 type molecular sieves as well for the purposes described herein. Desirably, the molecular sieve is selected from (a) MCM-49; (b) MCM-56; and (c) isotypes of MCM-49 and MCM-56, such as ITQ-2.

As used herein, the term "cyclohexylbenzene" shall mean benzene substituted by a single cyclohexyl group, unless specified to the contrary or the context clearly indicates otherwise. As used herein, the generic term "dicyclohexylbenzene" shall include 1,2-dicyclohexylbenzene, 1,3-dicyclohexylbenzene, 1,4-dicyclohexylbenzene, and mixtures and combinations of at least two thereof in any proportion. As used herein, the generic term "tricyclohexylbenzene" shall include 1,2,3-tricyclohexylbenzene, 1,2,4-tricyclohexylbenzene and 1,3,5-tricyclohexylbenzene, and combinations and mixtures thereof at any proportion. The generic term "polycyclohexylbenzene" shall include any of the dicyclohexylbenzene isomers and tricyclohexylbenzene isomers described above, and combinations and mixtures of at least two thereof in any proportion.

As used herein, "protonate" means "associate with a hydron." The term "hydron" includes proton, deuteron, and tritons. The hydrons used in the processes of the present disclosure may comprise, e.g., at least 95.00 mol % or at least 98.00 mol %, or at least 99.00 mol %, or at least 99.50 mol %, or at least 99.90 mol %, or at least 99.95 mol %, or at least 99.99 mol %, of protons. Preferably, the hydrons comprise proton, deuteron, and triton at percentages corresponding to their respective natural abundances. Unless specified to mean proton only, "$H^+$" as used in the present disclosure include, collectively, proton, deuteron ($D^+$) and triton ($T^+$).

Disclosed herein is an innovative process for quantifying the strength of an acid in a reaction medium. Many chemical reactions are conducted in a reaction medium in the presence of an acid. Such acid may be a reactant, a product, a by-product, an intermediate, or a catalyst in the reaction medium. The reaction equilibrium and kinetics of the desired reaction(s) and side reaction(s) can be affected to different degrees by the strength of the acid in the reaction medium. For example, the acid strength in the reaction medium can greatly affect the conversion of a product and the selectivity of a desired product. This is especially true in reactions involving an acid catalyst. As discussed below, in the cleavage reaction of organic hydroperoxides catalyzed by an acid, the strength of the acid determines partly the selectivity of the desired product (such as ketone). Furthermore, the strength of the same acid can vary significantly in different reaction media consisting of the same components at different concentrations, even if the acid concentration in the different media remains the same. Thus, in many of these reaction systems, it is of great interest to quantify the strength of the acid present in the reaction media as a function of the composition of the reaction media, so that the reaction media can be modified to achieve the desired reaction result according to the understanding of the relationship.

While acid strength in a reaction medium can be determined by conventional methods, such as titration and pH measurement in aqueous solutions and ion conductivity measurements, these methods are not sufficiently sensitive when the acid concentration is very low, and/or when the acid is present in an organic medium.

The process of the present disclosure can be advantageously used for quantifying the strength of an acid in an organic, inorganic or aqueous medium. Due to its high sensitivity, the process can be particularly useful to quantify the strength of an acid at low concentrations, such as concentrations not higher than AA ppm by weight, based on the total weight of the reaction medium, where AA can be, 5000, 4000, 3000, 2000, 1000, 900, 800, 700, 600, 500, 400, 300, 200, 180, 160, 150, 140, 120, 100, 90, 80, 70, 60, 50, 40, 30, 20, 10, 9, 8, 7, 6, 5, 4, 3, or 1.

The process of the present disclosure utilizes the high sensitivity of modern phosphorous-31 nuclear magnetic resonance ($^{31}$P NMR) technology. A description of $^{31}$P NMR technology that can be used in the present disclosure can be found, e.g., in "The Chemist's Companion: A Handbook of Practical Data, Techniques, and References" by A. J. Gordon and R. A. Ford (Eds), Wiley, 1972, pp. 293-296. Examples of NMR instruments that may be used in the process of the present disclosure include: Varian Innova 600 MHz NMR spectrometer and Bruker Biospin 400 MHz NMR spectrometer.

In the present process, to quantitatively measure the strength of an acid, a probe molecule, trimethylphosphine oxide (Me$_3$PO, TMPO), having the following formula, is used:

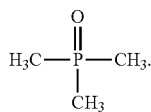

In the presence of acids, TMPO is protonated forming TMPOH$^+$, which is in rapid equilibrium:

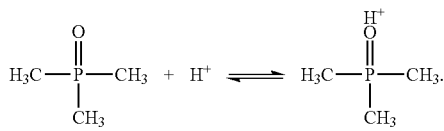

The protonation is reversible and the rate is faster than the NMR time-scale. Consequently, as shown in FIG. 1, a single, coalesced peak (rather than two separate peaks) is seen in the $^{31}$P NMR spectrum when the [H$^+$]/[TMPO] ratio is kept from 0 to 1.0, where [H$^+$] is the concentration of hydron in mole·liter$^{-1}$, and [TMPO] is the concentration of TMPO in the reaction medium in mole·liter$^{-1}$. As can be seen from FIG. 1, at a given total amount of TMPO and TMPOH$^+$ in a reaction medium sample, the higher the concentration of [H$^+$], the higher the concentration of TMPOH$^+$ will be, and the larger the chemical shift as measured will be for the sample.

Figure 2:
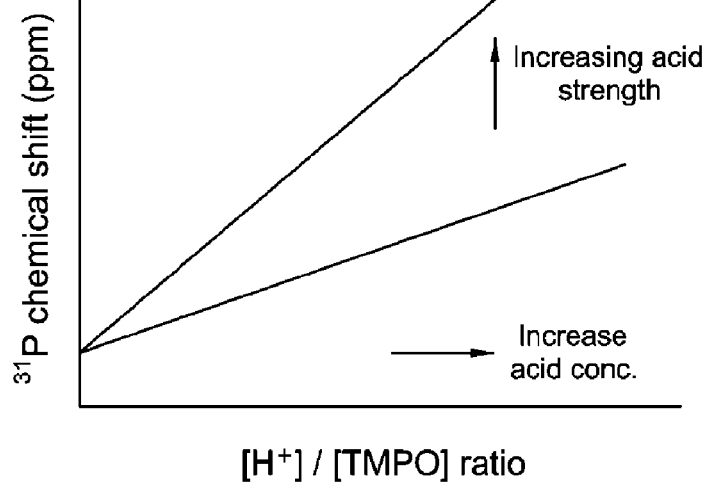
FIG. 2 depicts $^{31}$P NMR chemical shift as a function of [H$^+$]/[TMPO] ratios at two different acid strengths, demonstrating that the steeper the slope, the higher the acid strength.

The chemical shifts for the coalesced peak at various [H$^+$]/[TMPO] ratios can be measured. Plotting the chemical shift versus [H$^+$]/[TMPO] ratio data in a perpendicular x-y coordinate system followed by a linear fitting (such as by least-square fitting) gives a straight line. The slope of the line quantitatively represents the acid strength: the steeper the slope, the higher the acid strength (FIG. 2).

Using a known acid in a known media, such as aqueous sulfuric acid, as a standard, a quantitative acid strength scale can be established. The method is fast and easy to use, and can be used to guide the operation and optimization of conditions of reactions in which acid strength is an important variable. The method can be used for any liquid medium, as long as the medium does not react with the acid within the time needed to acquire the $^{31}$P NMR spectrum (~5 min).

When the process of the present disclosure is used to optimize a reaction condition, or to monitor the reaction conditions of a reaction system, samples to be studied are measured for the acid strength, and then compared against one or more standardized sample(s). The standardized sample has known concentration(s) of at least some of the components. A standardized sample can be prepared by (i) combining known components with known amounts; or (i) taking an aliquot of a reaction medium from an existing reaction system and determining the concentrations of the various concentrations of the components, optionally followed by altering the concentration of one or more components therein. The method of the present disclosure can be used to determine the effect of varying the concentration of a given component in a reaction medium on the strength of a particular acid in the reaction medium. This can be done, e.g., by (i) preparing a series of samples having multiple known components with different concentrations of one component but identical concentrations of other component(s); measuring the acid strength in these samples; and analyzing the relationship between concentration of that component and the acid strength. For example, to evaluate the reaction medium comprising cumene, acetone and phenol for the cleavage of cumene hydroperoxide catalyzed by H$_2$SO$_4$, one can determine the effect of phenol concentrations on the sulfuric acid strength in the medium by measuring the acid strength in a series of media having the same cumene and acetone concentrations but different phenol concentrations. The same can be done to determine the effect of acetone and cumene concentrations on sulfuric acid strength. The understanding gained on such effects can be used to guide the determination and adjustment of the concentrations of these components in a reaction medium in a real cumene hydroperoxide cleavage reactor. Alternatively, a database of the acid strength and component concentrations of a large number of samples with varying concentrations of each component may be established to guide the selection of a desired reaction medium with desired acid strength and composition, or the adjustment of the concentration(s) of component(s) in an existing medium to optimize the acid strength therein.

The process of the present disclosure can be advantageously used in optimizing and/or monitoring the reaction conditions of the cleavage of cyclohexyl-1-phenyl-1-hydroperoxide in the presence of a catalyst comprising sulfuric acid for producing phenol and cyclohexanone. The reaction medium of this reaction can comprise phenol, cyclohexanone, cyclohexylbenzene, water, by-products, and optionally other solvents. As discussed below, in this cleavage step, a high sulfuric acid strength in the reaction medium is conducive to a high selectivity of phenol and/or cyclohexanone. Thus, the process of the present disclosure described above can be advantageously used to identify the desired composition of the reaction medium with optimized acid strength therein, or monitor/modify the composition of an existing reaction medium to achieve better acid strength therein. In the process, the composition of the cleavage reaction mixture may be adjusted, for example, by changing the recycle rate of the cleavage effluent, changing the phenol, cyclohexanone and/or cyclohexylbenzene concentrations and the cleavage conditions so as to maximize the yield of phenol and cyclohexanone.

The cleavage process may form part of an integrated process for producing phenol from benzene in which the benzene is initially alkylated or hydroalkylated to produce cyclohexylbenzene and the cyclohexylbenzene is oxidized to produce cyclohexyl-1-phenyl-1-hydroperoxide. The ensuing description will therefore focus on this integrated process and methods to monitor the progress of the reaction conditions.

The contents of U.S. Patent application Ser. No. 61/729,019 filed Nov. 21, 2012; Title: Process for Producing Phenol and 61/885,336 filed Oct. 1, 2013; Title: Hydroalkylating Process are incorporated herein in their entirety.

Exemplary Production of Cyclohexylbenzene

In an integrated process for producing phenol and cyclohexanone from benzene, the benzene can be initially converted to cyclohexylbenzene by any conventional technique, including alkylation of benzene with cyclohexene in the presence of an acid catalyst, such as zeolite beta or an MCM-22 type molecular sieve described above, or by oxidative coupling of benzene to make biphenyl followed by hydrogenation of the biphenyl. However, in practice, the cyclohexylbenzene is desirably produced by contacting the benzene with hydrogen under hydroalkylation conditions in the presence of a hydroalkylation catalyst whereby the benzene undergoes the following Reaction-1 to produce cyclohexylbenzene (CHB):

(Reaction-1)

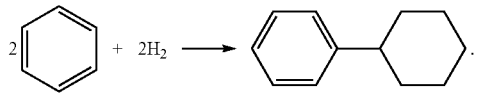

U.S. Pat. Nos. 6,730,625 and 7,579,511, WO2009/131769, and WO2009/128984 disclose processes for producing cyclohexylbenzene by reacting benzene with hydrogen in the presence of a hydroalkylation catalyst, the contents of all of which are incorporated herein by reference in their entirety.

Although the benzene hydroalkylation reaction is highly selective towards cyclohexylbenzene, the effluent from the hydroalkylation reaction may contain some dialkylated products, unreacted benzene and cyclohexane as noted above. The unreacted benzene may be recovered by distillation and recycled to a reactor. The lower effluent from the benzene distillation may be further distilled to separate a monocyclohexylbenzene product from dicyclohexylbenzene and other heavies. Depending on the quantity of dicyclohexylbenzene present in the reaction effluent, it may be desirable to either (a) transalkylate the dicyclohexylbenzene with additional benzene or (b) dealkylate the dicyclohexylbenzene to maximize the production of the desired monoalkylated species.

Transalkylation with additional benzene is desirably effected in a transalkylation reactor, separate from the hydroalkylation reactor, over a suitable transalkylation catalyst, such as a molecular sieve of the MCM-22 type, zeolite beta, MCM-68 (see U.S. Pat. No. 6,014,018), zeolite Y, zeolite USY, and mordenite. The transalkylation reaction is desirably conducted under at least partial liquid phase conditions, which suitably include a temperature of 100° C. to 300° C., a pressure of 800 kPa to 3500 kPa, a weight hourly space velocity of 1 hour$^{-1}$ to 10 hour$^{-1}$ on total feed, and a benzene/dicyclohexylbenzene weight ratio of 1:1 to 5:1.

Oxidation of Cyclohexylbenzene

After removal of the unreacted benzene and the polyalkylated benzenes and other heavy species, the cyclohexylbenzene produced in the hydroalkylation step is fed to an oxidizing step, which can be conducted in one or more oxidation reactor(s). Desirably, at least a portion of the cyclohexylbenzene contained in the oxidation feed is converted to cyclohexyl-1-phenyl-1-hydroperoxide, the desired hydroperoxide according to the following Reaction-2:

(Reaction-2)

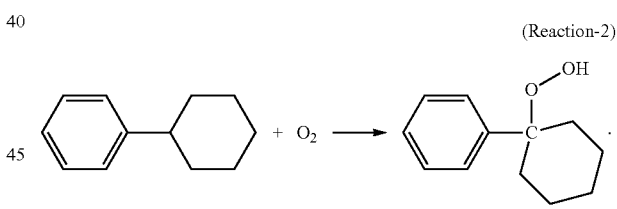

A feed supplied to the oxidizing step may comprise cyclohexylbenzene at a concentration in a range from C1 wt % to C2 wt %, based on the total weight of the feed introduced into the oxidation reactor, where C1 and C2 can be, independently, 10, 20, 30, 40, 50, 60, 70, 80, 90, 92, 94, 95, 96, 97, 98, 99, 99.5, or even 99.9, or even higher, as long as C1<C2. In addition, the feed to the oxidizing step may contain, based on the total weight of the feed, one or more of the following: (i) bicyclohexane at a concentration in a range from at 1 ppm to 1 wt %, such as from 10 ppm to 8000 ppm; (ii) biphenyl at a concentration in a range from 1 ppm to 1 wt %, such as from 10 ppm to 8000 ppm; (iii) phenylmethylcyclopentane, including one or more of 1-phenyl-1-methylcyclopentane, 1-phenyl-2-methylcyclopentane, and 1-phenyl-3-methylcyclopentane, at a total concentration in a range from 1 ppm to 2 wt %, such as from 10 ppm to 1 wt %; (iv) phenol at a concentration no greater than 1000 ppm, such as no greater than 100 ppm; and (v) olefins or alkene benzenes such as phenylcyclohexene at no greater than 1000 ppm (or no greater than 800, 600, 500, 400, 300, 200, 100, 80, 60, 50, 40, 20, 10, 8, 6, 5, 4, 2, 1 ppm), which is advantageously reduced by using the process disclosed herein.

The oxidizing step may be accomplished by contacting an oxygen-containing gas, such as air and various derivatives of air, with the feed comprising cyclohexylbenzene. A stream of pure $O_2$, air, or other $O_2$-containing mixtures may be pumped through the cyclohexylbenzene-containing feed in an oxidation reactor such as a bubble column to effect the oxidation.

The oxidation may be conducted in the absence or presence of a catalyst. Examples of suitable oxidation catalysts include those having a structure of formula (FC-I), (FC-II), or (FC-III) below, which would act as free radical promoters in the oxidation reaction:

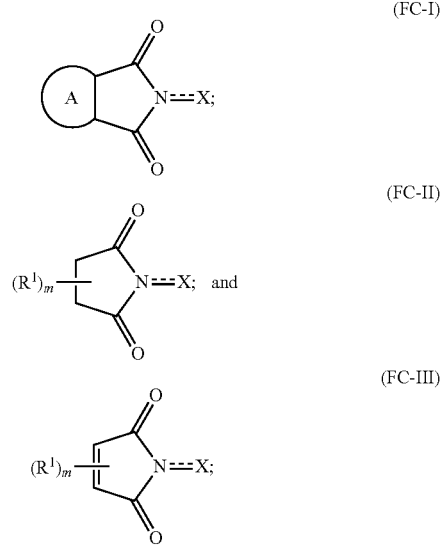

where:

A represents a ring optionally comprising a nitrogen, sulfur, or oxygen in the ring structure, and optionally substituted by an alkyl group, an alkenyl group, a halogen, or a N-, S-, or O-containing group or other group;

X represents a hydrogen, an oxygen, a hydroxyl group, or a halogen;

$R^1$, the same or different at each occurrence, independently represents a halogen, a N-, S-, or O-containing group, or a linear or branched acyclic alkyl or cyclic alkyl group having 1 to 20 carbon atoms, optionally substituted by an alkyl, an alkenyl, a halogen, or a N-, S-, or O-containing group or other group; and m is 0, 1 or 2.

Examples of particularly suitable catalysts for the oxidation step include those represented by the following formula (FC-IV):

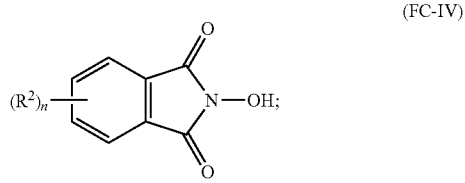

where:

$R^2$, the same or different at each occurrence, independently represents a halogen, a N-, S-, or O-containing group, or an optionally substituted linear or branched acyclic alkyl or cyclic alkyl group having 1 to 20 carbon atoms; and n is 0, 1, 2, 3, or 4.

Especially suitable catalyst having the above formula (FC-IV) for the oxidation step is NHPI (N-hydroxy phthalic imide). Other suitable catalysts are described in U.S. Pat. No. 6,720,462, which is incorporated herein by reference. Specific, non-limiting examples of other suitable catalysts include: 4-amino-N-hydroxyphthalimide; 3-amino-N-hydroxyphthalimide, tetrabromo-N-hydroxyphthalimide; tetrachloro-N-hydroxyphthalimide; N-hydroxyhetimide; N-hydroxyhimimide; N-hydroxytrimellitimide; N-hydroxybenzene-1,2,4-tricarboximide; N,N'-dihydroxy (pyromellitic diimide); N,N'-dihydroxy(benzophenone-3,3', 4,4'-tetracarboxylic diimide); N-hydroxymaleimide; pyridine-2,3-dicarboximide; N-hydroxysuccinimide; N-hydroxy (tartaric imide); N-hydroxy-5-norbornene-2,3-dicarboximide; exo-N-hydroxy-7-oxabicyclo[2.2.1]hept-5-ene-2,3-dicarboximide; N-hydroxy-cis-cyclohexane-1,2-dicarboximide; N-hydroxy-cis-4-cyclohexene-1,2 dicarboximide; N-hydroxynaphthalimide sodium salt; N-hydroxy-o-benzenedisulphonimide; and N,N',N''-trihydroxy-isocyanuric acid.

Non-limiting examples of suitable reaction conditions of the oxidizing step include a temperature from 70° C. to 200° C., such as 90° C. to 130° C., and a pressure of 50 kPa to 10,000 kPa. A basic buffering agent may be added to react with acidic by-products that may form during the oxidation. In addition, an aqueous phase may be introduced into the oxidation reactor. The reaction may take place in a batch or continuous flow fashion.

The reactor used for the oxidizing step may be any type of reactor that allows for the oxidation of cyclohexylbenzene by an oxidizing agent, such as molecular oxygen. A particularly advantageous example of the suitable oxidation reactor is a bubble column reactor capable of containing a volume of the reaction media and bubbling an $O_2$-containing gas stream (such as air) through the media. For example, the oxidation reactor may comprise a simple, largely open vessel with a distributor inlet for the oxygen-containing stream. The oxidation reactor may have means to withdraw a portion of the reaction media and pump it through a suitable cooling device and return the cooled portion to the reactor, thereby managing the heat generated in the reaction. Alternatively, cooling coils providing indirect cooling, e.g., by cooling water, may be operated within the oxidation reactor to remove at least a portion of the generated heat. Alternatively, the oxidation reactor may comprise a plurality of reactors in series, each operating at the same or different conditions selected to enhance the oxidation reaction of reaction media with different compositions. The oxidation reactor may be operated in a batch, semi-batch, or continuous flow manner well known to those skilled in the art.

Treatment of the Oxidation Product Before Cleavage

Desirably, the oxidation product exiting the oxidation reactor contains cyclohexyl-1-phenyl-1-hydroperoxide at a concentration in a range from Chp1 wt % to Chp2 wt %, based on the total weight of the oxidation product, where Chp1 and Chp2 can be, independently, 5, 10, 15, 20, 25, 30, 35, 40, 45, 50, 55, 60, 65, 70, 75, 80, as long as Chp1<Chp2. The oxidation product may further comprise (i) an oxidation catalyst described above; and (ii) unreacted cyclohexylbenzene at a concentration in a range from Cchb1 wt % to Cchb2 wt %, based on the total weight of the oxidation product, where Cchb1 and Cchb2 can be, independently, 20, 25, 30, 35, 40, 45, 50, 55, 60, 65, 70, 75, 80, 85, 90, 95, as long as Cchb1<Cchb2.

In addition, the oxidation product may contain one or more hydroperoxides other than cyclohexyl-1-phenyl-1-hydroperoxide generated as a byproduct of the oxidation reaction of cyclohexylbenzene, or as the oxidation product of some oxidizable component other than cyclohexylbenzene that may have been contained in feed supplied to the oxidizing step, such as cyclohexyl-2-phenyl-1-hydroperoxide, and cyclohexyl-3-phenyl-1-hydroperoxide. These undesired hydroperoxides are desirably at a total concentration of at most 5 wt %, such as at most 3 wt %, 2 wt %, 1 wt %, or even 0.1 wt %.

The oxidation product contains the oxidation catalyst, such as NHPI, and certain by-products. Thus, it may be desirable to wash the oxidation product to remove the by-products and/or the catalyst before cleavage by using an aqueous dispersion. For example, a basic aqueous dispersion, such as a solution of one or more of alkali or alkali earth carbonates, alkali or alkali earth bicarbonates, alkali or alkali earth hydroxides, ammonium hydroxide, may be used to wash the oxidation product to extract NHPI or other similar imide-based catalysts from the oxidation product. In so doing, water concentration in the oxidation product thus washed will increase.

Alternatively, to reclaim the oxidation catalyst from the oxidation product, the oxidation product may be subjected to contacting with a solid sorbent in the form of particles in a slurry or a fixed bed, such as solid alkali or alkali earth metal carbonates, alkali or alkali earth metal bicarbonates, alkali or alkali earth metal hydroxide, molecular sieves, activated carbon, and the like. After separation, the sorbent may be washed using a polar solvent, such as water, acetone, an alcohol, and the like, to reclaim the oxidation catalyst, which can be purified and recycled to the oxidation reactor.

In the process disclosed herein, at least a portion of the cyclohexylbenzene hydroperoxide in the oxidation product is subjected to a cleavage reaction, desirably in the presence of a catalyst such as an acid, whereby it is converted into phenol and/or cyclohexanone.

At least a portion of the oxidation product may be fed into the cleavage reactor without substantial alteration of the concentration of cyclohexylbenzene hydroperoxide and/or cyclohexylbenzene therein. Thus, where the concentration of cyclohexylbenzene in the oxidation product is CCHB(op) wt % based on the total weight of the oxidation product, and the concentration of cyclohexylbenzene in the cleavage feed is CCHB(cf) wt % based on the total weight of the cleavage feed before any material other than those contained in the oxidation product is added, the following relationship may be satisfied: $(CCHB(op)-CCHB(cf))/CCHB(cf) \leq 0.05$. The oxidation product may be flashed in a vessel at an absolute pressure in a range from Pf1 kPa to Pf2 kPa to remove a portion of water contained therein, where Pf1 and Pf2 can be, independently, 2.50, 2.67, 3.00, 3.50, 4.00, 4.50, 5.00, 5.50, 6.00, 6.50, 6.67, 7.00, 7.50, 8.00, 8.50, 9.00, 10.00, 11.00, 12.00, 13.00, 13.33, 14.00, 15.00, 16.00, 17.00, 18.00, 19.00, 20.00, 25.00, 30.00, 35.00, 40.00, 45.00, or 50.00, as long as Pf1<Pf2. Desirably, the oxidation product is flashed in a vessel, such as a flashing drum, at an absolute pressure in a range from 6.67 kPa (50 torr) to 13.33 kPa (100 torr). During the flashing step, other low boiling components that may be present in the oxidation product, such as lower acids (e.g., formic acid, acetic acid, and the like) and low boiling point hydrocarbons (e.g., benzene, cyclohexane, methylcyclopentane, and the like), may be at least partially removed along with water, resulting in a cleaner cleavage feed.

Desirably, at least a portion of the oxidation product is not fed into the cleavage reactor before the concentration of cyclohexylbenzene therein is significantly reduced, and hence, the concentration of cyclohexylbenzene hydroperoxide is significantly increased. Thus, where the concentration of cyclohexylbenzene in the oxidation product is CCHB(op) wt % based on the total weight of the oxidation product, and the concentration of cyclohexylbenzene in the cleavage feed is CCHB(cf) wt % based on the total weight of the cleavage feed before any material other than those contained in the oxidation product is added, the following relationship may be satisfied: $R1<(CCHB(op)-CCHB(cf))/CCHB(op) \leq R2$, where R1 and R2 are, independently, 0.05, 0.08, 0.10, 0.12, 0.14, 0.15, 0.18, 0.20, 0.25, 0.30, 0.35, 0.40, 0.45, 0.50, 0.55, 0.60, 0.70, 0.75, 0.80, 0.85, or even 0.90, as long as R1<R2. Desirably, R1=0.25, and R2=0.75. The reduction of cyclohexylbenzene concentration from the oxidation product before cleavage is particularly advantageous where liquid acid, such as sulfuric acid, is used as the cleavage catalyst. Without intending to be bound by a particular theory, it is believed that this is because the liquid acid tends to have low solubility in cyclohexylbenzene, and the desired catalytic effect of the liquid acid can be significantly reduced as a result of high cyclohexylbenzene concentration. Experimental data have shown that partial removal of cyclohexylbenzene concentration from the oxidation product before it is fed to the cleavage step can significantly improve the selectivity of the cleavage reaction to form the desired products, i.e., cyclohexanone and/or phenol.

Because cyclohexylbenzene hydroperoxide is prone to decomposition at an elevated temperature, e.g., at above 150° C., the removal of cyclohexylbenzene from the oxidation product should be conducted at a relatively low temperature, e.g., no higher than 150° C., or no higher than 140° C., or no higher than 130° C., or no higher than 120° C., or even no higher than 110° C. Cyclohexylbenzene has a high boiling point (239° C. at 101 kPa). Thus, at the acceptable cyclohexylbenzene-removal temperature, cyclohexylbenzene tends to have very low vapor pressure. Accordingly, desirably, to effectively remove a meaningful amount of cyclohexylbenzene from the oxidation product, the oxidation product is subjected to a very low absolute pressure, e.g., in a range from Pc1 kPa to Pc2 kPa, where Pc1 and Pc2 can be, independently, 0.13, 0.15, 0.20, 0.25, 0.26, 0.30, 0.35, 0.39, 0.40, 0.45, 0.50, 0.60, 0.65, 0.70, 0.75, 0.80, 0.85, 0.90, 0.95, 1.00, 1.33, 1.50, 2.00, 2.50, 2.66, as long as Pc1<Pc2. Desirably, Pc1=0.27, and Pc2=2.00.

Where cyclohexylbenzene is partly removed from the oxidation product before cleavage, water contained in the oxidation product can be at least partly removed at the same time and in the same vessel where the cyclohexylbenzene is partly removed at a low absolute internal pressure.

Because of the very low absolute pressure required for effective cyclohexylbenzene removal, it is highly desired that before the oxidation product is subjected to cyclohexylbenzene removal, components with boiling points substantially lower than cyclohexylbenzene, such as water, benzene, cyclohexane, lower acids, and the like, contained in the oxidation product are removed at a relatively high pressure before the mixture is subjected to the very low pressure required for cyclohexylbenzene removal, such that the vacuum pump used for imparting the very low pressure is not overwhelmed. To that end, the oxidation product, upon exiting the oxidation reactor, may be first flashed in a first vessel such as a flashing drum at an absolute pressure in a range from Pf1 kPa to Pf2 kPa, where Pf1 and Pf2 can be, independently, 2.67, 3.00, 3.50, 4.00, 4.50, 5.00, 6.00, 7.00, 8.00, 9.00, 10.00, 11.00, 12.00, 13.00, 13.33, 14.00, 15.00, 20.00, 25.00, 30.00, 35.00, 40.00, 45.00, 50.00, as long as Pf1<Pf2, where a majority of the water contained in the oxidation product is removed, and desirably less than AA % of the cyclohexylbenzene contained in the oxidation product is removed, the percentage based on the total amount of cyclohexylbenzene contained in the oxidation product, where AA can be: 5, 4, 3, 2, 1, 0.8, 0.6, 0.5, 0.4, 0.3, 0.2, or 0.1.

Removal of cyclohexylbenzene from the oxidation product can be advantageously conducted in a concentrator comprising one or more falling film evaporator(s), such as those descried in co-pending, co-assigned U.S. provisional patent application Ser. No. 61/841,072 filed on Jun. 28, 2013 and entitled "Process for Concentrating a Mixture Containing Organic Hydroperoxide." The concentrator advantageously employs one or more falling film evaporators operating in parallel and/or in series operating under very low absolute pressure(s) described above. Because cyclohexylbenzene has a lower boiling point than cyclohexylbenzene hydroperoxide, a portion of the cyclohexylbenzene contained in the oxidation product evaporates under the very low pressure and is enriched in the vapor phase, condensed and collected for recycling back to the oxidizing step. Since by-products produced in the oxidizing step tend to accumulate in the condensed cyclohexylbenzene stream, a washing or extracting treatment of the condensed cyclohexylbenzene using an aqueous dispersion or other agent may be desired before the recycling thereof to the oxidizing step in order to prevent interference of the oxidation reaction of cyclohexylbenzene by the accumulated oxidation by-products. Such aqueous dispersion may be acidic, basic, or neutral in pH. The washing or extracting treatment may advantageously include a first step of chemical wash followed by a step of washing using water only. The thus washed reclaimed cyclohexylbenzene may be dried by using a water sorbent, such as a 3 Å molecular sieve before being recycled to oxidizing step. Alternatively, because water up to a certain amount is tolerated in the oxidation reactor, the thus washed cyclohexylbenzene, which contains a significant amount of water, may be fed to the oxidizing step directly without drying as at least a portion of the total feed, thus eliminating the cost of drying.

As an alternative approach, water removal of the optionally treated oxidation product can be effected by passing the liquid mixture through a water sorbent, such as a 3 Å molecular sieve. Desirably, the water sorbent also adsorbs the oxidation catalyst, which may be reclaimed by washing with a polar solvent.

Additionally or alternatively, after water removal and before or after partial cyclohexylbenzene removal, all or a portion of the oxidation product may be cooled to cause crystallization of the unreacted imide oxidation catalyst, which may then be separated either by filtration or by scraping from a heat exchanger surface used to effect the crystallization.

Cleavage Reaction

As discussed above, the process for making phenol and cyclohexanone from benzene includes cleaving at least a portion of the cyclohexylbenzene hydroperoxide contained in the oxidation product in the presence of an acid catalyst to produce a cleavage reaction mixture comprising the acid catalyst, phenol, and cyclohexanone. As used herein, "cleaving" means causing a cleavage reaction to occur. In the cleavage reaction, at least a portion of the desired cyclohexyl-1-phenyl-1-hydroperoxide desirably decomposes in high selectivity to cyclohexanone and phenol, and further, other hydroperoxides present may decompose to form various products, discussed below.

The acid catalyst may be at least partially soluble in the cleavage reaction mixture, stable at a temperature of at least 185° C. and has a lower volatility (higher normal boiling point) than cyclohexylbenzene. The acid catalyst may also be at least partially soluble in the treated cleavage reaction mixture.

Acid catalysts include, but are not limited to, Bronsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

As a result of potentially high amounts of cyclohexylbenzene in the cleavage reaction mixture, considerably higher than cumene in the Hock process material undergoing a cleavage reaction, it may be convenient to use more acid catalyst to effect the cleavage reaction than believed optimal in the Hock process, to at least partially overcome the insolubility of the acid in the cleavage reaction mixture. However, lower amounts of acid catalyst may be applied, with appropriate additional cleavage reactor volume and residence time of the cleavage reaction mixture in the cleavage reactor to obtain high hydroperoxide conversion.

The cleavage reaction occurs under suitable cleavage conditions such as a temperature of at least 20° C. and no greater than 200° C., or at least 40° C. and no greater than 120° C., and a pressure of at least 1 and no greater than 370 psig (at least 7 kPa, gauge and no greater than 2,550 kPa, gauge), or at least 14.5 psig and no greater than 145 psig (at least 100 kPa, gauge and no greater than 1,000 kPa, gauge) such that the cleavage reaction mixture is completely or predominantly in the liquid phase during the cleavage reaction.

The cleavage reaction mixture may contain the acid catalyst at a concentration in a range from Cac1 ppm to Cac2 ppm by weight of the total weight of the cleavage reaction mixture, where Cac1 and Cac2 can be, independently, 10, 20, 30, 40, 50, 60, 80, 100, 150, 200, 250, 300, 350, 400, 450, 500, 600, 700, 800, 900, 1000, 1500, 2000, 2500, 3000, 3500, 4000, 4500, or even 5000, as long as Cac1<Cac2. Desirably, Cac1 is 50, and Cac2 is 200.

Conversion of any hydroperoxide, such as cyclohexyl-1-phenyl-1-hydroperoxide, and conveniently all cyclohexyl-1-phenyl-1-hydroperoxide and other hydroperoxides, may be very high in the cleavage reaction, e.g., at least 90.0 wt %, or at least 95.0 wt %, or at least 98.0 wt %, or at least 99.0 wt %, or at least 99.5 wt %, or at least 99.9 wt %, or even 100 wt %, the percentage conversion based on the weight of a given specie of hydroperoxide, or of all cyclohexyl-1-phenyl-1-hydroperoxide, and other hydroperoxides present in the at least a portion of the oxidation product undergoing the cleavage reaction. This is desirable because any hydroperoxide, even the cyclohexyl-1-phenyl-1-hydroperoxide, becomes a contaminant in the cleavage reaction mixture and treated cleavage reaction mixture, discussed below. Hydroperoxides cause undesired chemistry when decomposed under uncontrolled conditions outside the cleavage reaction, or if thermally decomposed under the conditions in a distillation column.

The major products of the cleavage reaction of cyclohexyl-1-phenyl-1-hydroperoxide are phenol and cyclohexanone according to the following desired Reaction-3:

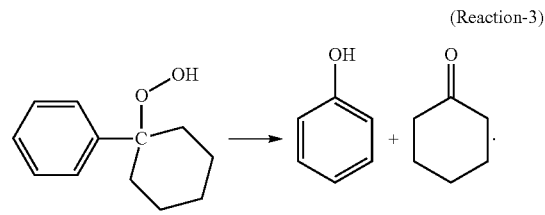

(Reaction-3)

Desirably, each mole of cyclohexyl-1-phenyl-1-hydroperoxide produces one mole of phenol and one mole of cyclohexanone. However, due to side reactions, the selectivity of the cleavage reaction of phenol can range from Sph1% to Sph2% and the selectivity of cyclohexanone can range from Sch$_1$% to Sch2%, where Sph1, Sph2, Sch1, and Sch2 can be, independently, 85, 87, 88, 89, 90, 91, 92, 93, 94, 95, 96, 97, 98, 99, or even 99.5, as long as Sph1<Sph2, and Sch1<Sch2.

Besides the cleavage feed comprising cyclohexylbenzene hydroperoxide, cyclohexylbenzene and other components originating directly from the oxidation product, the cleavage reaction mixture may further comprise other added materials, such as the cleavage catalyst, a solvent, and one or more products of the cleavage reaction such as phenol and cyclohexanone recycled from the cleavage reaction effluent, or from a downstream separation step. Thus, the cleavage reaction mixture inside the cleavage reactor may comprise, based on the total weight of the cleavage reaction mixture: (i) phenol at a concentration from Cph1 wt % to Cph2 wt %, where Cph1 and Cph2 can be, independently, 20, 25, 30, 35, 40, 45, 50, 55, 60, 65, 70, 75, or 80, as long as Cph1<Cph2; (ii) cyclohexanone at a concentration from Cch1 wt % to Cch2 wt %, where Cch1 and Cch2 can be, independently, 20, 25, 30, 35, 40, 45, 50, 55, 60, 65, 70, 75, or 80, as long as Cch1<Cch2; (iii) cyclohexylbenzene at a concentration from Cchb1 wt % to Cchb2 wt %, where Cchb1 and Cchb2 can be, independently, 5, 8, 9, 10, 12, 14, 15, 18, 20, 22, 24, 25, 26, 28, 30, 35, 40, 45, 50, 55, 60, 65, 70, as long as Cchb1<Cchb2.

As used herein, a "contaminant" or a "contaminant byproduct" may include any unwanted hydrocarbon or oxygenated hydrocarbon component in the cleavage reaction mixture or the neutralized cleavage mixture, or any portion of either; that is anything other than phenol, cyclohexanone, and cyclohexylbenzene. They are unwanted because their presence indicates a decreased yield of desired product phenol and cyclohexanone from cyclohexylbenzene, or they cause difficulties in the separation and purification of phenol, cyclohexanone or unconverted cyclohexylbenzene, or some combination thereof. A contaminant in the cleavage reaction mixture, or the neutralized cleavage mixture, or any portion thereof may have been produced in any element of the processes, or may have been contained in the feed comprising cyclohexylbenzene undergoing oxidation. For example, a contaminant may be present in the cleavage reaction mixture as a result of one or more of: (i) it was included with the cyclohexylbenzene (e.g., as a byproduct of production using hydroalkylation or alkylation); (ii) it was produced in oxidation of the feed comprising cyclohexylbenzene, and potentially the oxidation of an oxidizable component from (i); and/or (iii) it was produced in the cleavage reaction of at least a portion of the oxidation product from (ii).

The reactor used to effect the cleavage reaction (i.e., the cleavage reactor) may be any type of reactor known to those skilled in the art. For example, the cleavage reactor may be a simple, largely open vessel operating in a near-continuous stirred tank reactor mode, or a simple, open length of pipe operating in a near-plug flow reactor mode. Alternatively, the cleavage reactor may comprise a plurality of reactors in series, each performing a portion of the conversion reaction, optionally operating in different modes and at different conditions selected to enhance the cleavage reaction at the pertinent conversion range. The cleavage reactor may be a catalytic distillation unit.

The cleavage reactor may be operable to transport a portion of the contents through a cooling device and return the cooled portion to the cleavage reactor, thereby managing the exothermicity of the cleavage reaction. Alternatively, the reactor may be operated adiabatically. Cooling coils operating within the cleavage reactor(s) remove any heat generated.

The cleavage reaction product exiting cleavage reactor may comprise, based on the total weight of the cleavage reaction mixture: (i) phenol at a concentration from Cph3 wt % to Cph4 wt %, where Cph1 and Cph2 can be, independently, 20, 25, 30, 35, 40, 45, 50, 55, 60, 65, 70, 75, or 80, as long as Cph3<Cph4; (ii) cyclohexanone at a concentration from Cch3 wt % to Cch4 wt %, where Cch3 and Cch4 can be, independently, 20, 25, 30, 35, 40, 45, 50, 55, 60, 65, 70, 75, or 80, as long as Cch3<Cch4; (iii) cyclohexylbenzene at a concentration from Cchb3 wt % to Cchb4 wt %, where Cchb3 and Cchb4 can be, independently, 5, 8, 9, 10, 12, 14, 15, 18, 20, 22, 24, 25, 26, 28, 30, 35, 40, 45, 50, 55, 60, 65, 70, as long as Cchb3<Cchb4.

At least a portion of the cleavage reaction mixture may be subjected to a neutralization reaction, which may include all or some fraction of the cleavage reaction mixture as directly produced without undergoing any separation (e.g., some fraction resulting from diverting some amount of the cleavage reaction mixture as directly produced to another disposition, such as temporary storage). Thus, the at least a portion of the cleavage reaction mixture may have the same composition as the cleavage reaction mixture. Further, all or some of the cleavage reaction mixture as directly produced may undergo one or more separations, and an appropriate product of that separation (or separations), now modified in composition relative the cleavage reaction mixture as directly produced, may provide the at least a portion of the cleavage reaction mixture subjected to the neutralization reaction.

The cyclohexylbenzene contained in the cleavage reaction product can be separated from other major components, such as phenol and cyclohexanone by, e.g., distillation. The separated cyclohexylbenzene can then be treated and/or purified, e.g., by washing using an aqueous dispersion, before being delivered to the oxidation step along with cyclohexylbenzene supplied from other sources, such as fresh cyclohexylbenzene produced from the hydroalkylation reactor and a recycle cyclohexylbenzene stream from the cyclohexylbenzene hydroperoxide concentrator.

Quantitative Measurement of Acid Strength in the Cleavage Medium

The method of the present disclosure described above can be used to determine the strength of sulfuric acid ($H_2SO_4$) in the reaction medium comprising cyclohexylbenzene, phenol, cyclohexanone, water, and cyclohexylbenzene hydroperoxide. The results agreed with cleavage experimental observations very well: i.e., yield to phenol and cyclohexanone is improved significantly as the acid strength increases from 18 to 30, reaching 98+%. Thus, the method of the present disclosure can be used to determine the optimal concentration(s) of cyclohexylbenzene, cyclohexanone, phenol, water, and the like, in the reaction medium for cyclohexylbenzene hydroperoxide cleavage. Alternatively, the method can be used to monitor the reaction conditions, and/or guide the adjustment of the reaction conditions, including but not limited to the concentrations of various components.

Desirable strength of $H_2SO_4$ in the cleavage reaction medium, determined as the slope of the linear fit of the chemical shift versus [H$^+$]/[TMPO] obtained according to the procedure above, is from AC1 to AC2, where AC1 and AC2 can be, independently, −20, −15, −10, −8, −6, −5, −4, −2, 0, 2, 4, 5, 8, 10, 15, 20, 25, 30, 35, 40, 45, 50, 55, 60, 65, 70, 75, 80, as long as AC1<AC2.

Contaminant Treatment

As discussed above, the cleavage reaction products may comprise one or more contaminants. The processes may further comprise contacting at least a portion of a contaminant with an acidic material to convert at least a portion of the contaminant to a converted contaminant, thereby producing a modified reaction mixture. Detailed description of the contaminant treatment process can be found, e.g., in International Publication WO2012/036822A1, the relevant content of which is incorporated herein by reference in its entirety.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon-6 and nylon-6,6.

The phenol produced through the processes disclosed herein may be used, for example, to produce phenolic resins, bisphenol A, ε-caprolactam, adipic acid, and/or plasticizers.

While the present invention has been described and illustrated by reference to particular aspects disclosed herein, those of ordinary skill in the art will appreciate that the invention lends itself to variations not necessarily illustrated herein. For this reason, then, reference should be made solely to the appended claims for purposes of determining the true scope of the present invention.

The contents of all references cited herein are incorporated by reference in their entirety.

Non-limiting aspects and/or embodiments of the processes of the present disclosure include those paragraphs noted below from E1 to E30:

E1. A method to determine the strength of an acid in a medium comprising:
  (I) providing multiple samples comprising trimethylphosphine oxide (TMPO), the acid, and the medium, the multiple samples having different [H⁺]/[TMPO] ratios of less than 1.0, where [H⁺] is the concentration of protons in the sample in mole·liter$^{-1}$, and [TMPO] is the concentration of TMPO used in the sample in mole·liter$^{-1}$; and
  (II) measuring the $^{31}$P chemical shifts of the multiple samples by $^{31}$P NMR.

E2. The method of E1, further comprising:
  (III) determining the acid strength in the medium by plotting the $^{31}$P chemical shift (ppm) versus the [H⁺]/[TMPO] ratio.

E3. The method of E2, wherein the step (III) of determining the acid strength comprises:
  (IIIa) drawing $^{31}$P chemical shift versus [H⁺]/[TMPO] data points in a coordinate system;
  (IIIb) providing a linear fitting of the data points; and
  (IIIc) determining the slope of the linear fitting.

E4. The method of any of E1 to E3, wherein the medium comprises at least one of (i) a solvent, (ii) a reactant, (iii) water, and (iv) a product of a reaction system.

E5. The method of E4, wherein the reaction system includes a chemical reaction dependent on the acid strength of the acid.

E6. The method of E4 or E5, wherein the reaction system is catalyzed by the acid.

E7. The method of any of E4, E5, and E6, wherein the reaction system includes a cleavage reaction of a hydroperoxide compound.

E8. The method of E7, wherein the medium comprises cyclohexylbenzene, cyclohexanone, phenol, water or combinations of two or three thereof.

E9. The method of E7, wherein the medium comprises cumene, acetone, phenol, water, or combinations of two or three thereof E10. The method of any of E1 to E9, wherein the acid is sulfuric acid.

E11. The method of any of E1 to E10, wherein in step (II), the $^{31}$P NMR chemical shift data is referenced against $H_3PO_4$.

E12. The method of any of the E1 to E11, wherein the medium has:
  a cyclohexylbenzene concentration in a range from 5 wt % to 90 wt %;
  a phenol concentration in a range from 0 wt % to 90 wt %;
  a cyclohexanone concentration in a range from 0 wt % to 90 wt %; and
  a water concentration in a range from 0 ppm to 1 wt % (10000 ppm by weight);
  where all concentrations are based on the total weight of the medium.

E13. The method of E12, wherein the strength of the acid varies from −10 to 60.

E14. A method for optimizing reaction conditions of a reaction system, the method comprising:
  (A) providing a sample comprising a reaction medium and an acid;
  (B) combining trimethylphosphine oxide (TMPO) with aliquots of the sample to provide a series of mixtures containing both TMPO and protonated TMPO and having different [H⁺]/[TMPO] ratios of less than 1.0;
  (C) measuring the chemical shifts of the mixtures by $^{31}$P NMR;
  (D) plotting the chemical shifts against the [H⁺]/[TMPO] ratios to determine the slope of a linear fit;
  (E) comparing the slope of the linear fit to that of a standardized sample comprising the same components of the reaction medium; and
  (F) determining whether one or more components of the reaction medium and/or amount thereof should be adjusted to provide for a desired acid strength.

E15. The method of E14, wherein the reaction medium comprises at least one of (i) a solvent, (ii) a reactant, (iii) water, and (iv) a product of a reaction system.

E16. The method of E15, wherein the reaction system includes a chemical reaction dependent on the acid strength of the acid.

E17. The method of E15 or E16, wherein the reaction system is catalyzed by the acid.

E18. The method of any of E14 through E17, wherein the reaction system includes a cleavage reaction of a hydroperoxide compound.

E19. The method of E18, wherein the reaction medium comprises cyclohexylbenzene, cyclohexanone, phenol, water, or combinations of two or three thereof E20. The method of E14, wherein the reaction medium comprises cumene, acetone, phenol, water, or combinations of two or three thereof.

E21. The method any of E14 through E20, wherein the acid is sulfuric acid.

E22. The method of any of E14 through E21, wherein in step (C), the $^{31}$P NMR chemical shift data is referenced against $H_3PO_4$.

E23. The method of any of E14 through E19, E22 and E23, wherein the medium has:
  a cyclohexylbenzene concentration in a range from 5 wt % to 90 wt %;
  a phenol concentration in a range from 0 wt % to 90 wt %;
  a cyclohexanone concentration in a range from 0 wt % to 90 wt %; and
  a water concentration in a range from 0 ppm to 1 wt % (1000 ppm) by weight;

where all concentrations are based on the total weight of the medium.

E24. The method of E23, wherein the strength of the acid varies from −10 to 60.

E25. A method for monitoring a process for producing phenol and cyclohexanone, the process comprising:
(a) providing a cleavage feed containing greater than 10 wt % and no greater than 95 wt % cyclohexyl-1-phenyl-1-hydroperoxide, and at least 5 wt % and less than 90 wt % cyclohexylbenzene;
(b) mixing the cleavage feed with at least phenol, cyclohexanone, water, and sulfuric acid, to produce a cleavage reaction mixture containing from 10 wt % to 80 wt % phenol, from 10 wt % to 60 wt % cyclohexanone, from 0.5 wt % to 10 wt % cyclohexyl-1-phenyl-1-hydroperoxide, from 3 wt % to 60 wt % cyclohexylbenzene, from 0.01 wt % to 4 wt % water, and from 10 ppm to 1000 ppm sulfuric acid, where all concentrations are based on the total weight of the cleavage reaction mixture; and
(c) reacting the cleavage reaction mixture at a temperature from 20° C. and to 90° C. for a time sufficient to convert at least 50% of the cyclohexyl-1-phenyl-1-hydroperoxide in the cleavage reaction mixture and produce a cleavage effluent containing phenol and cyclohexanone;
wherein the process is monitored by:
(m1) taking a sample of the cleavage reaction mixture;
(m2) combining trimethylphosphine oxide (TMPO) with a series of aliquots of the sample to provide a series of mixtures containing both TMPO and protonated TMPO and having different $[H^+]/[TMPO]$ ratios of less than 1.0;
(m3) measuring the chemical shifts of the mixtures by $^{31}P$ NMR;
(m4) plotting the chemical shifts against the $[H^+]/[TMPO]$ ratios to determine the slope of the linear fit;
(m5) comparing the slope of the linear fit to that of a standardized sample comprising the same components of the reaction medium; and
(m6) determining whether one or more components of the cleavage mixture and/or amount thereof should be adjusted to provide for a desired acid strength.

E26. The method of E25, wherein the step (m4) of determining the linear fit comprises:
(m4a) drawing $^{31}P$ chemical shift versus $[H^+]/[TMPO]$ data points in a coordinate system;
(m4b) providing a linear fitting of the data points; and
(m4c) determining the slope of the linear fitting.

E27. The method of either E25 or E26, wherein in step (m3), the $^{31}P$ NMR chemical shift data is referenced against $H_3PO_4$.

E28. The method of E27, wherein the strength of the acid varies from −10 to 60.

E29. A method to monitor a process for a process for producing phenol and cyclohexanone, the process comprising:
(a) providing a cleavage feed containing cyclohexyl-1-phenyl-1-hydroperoxide;
(b) mixing the cleavage feed with at least phenol and cyclohexanone to produce a cleavage reaction mixture; and
(c) reacting the cleavage reaction mixture in the presence of a sulfuric acid catalyst under conditions to maintain the weight ratio of phenol to cyclohexanone in the cleavage reaction mixture in excess of 1:1 and to convert part of the cyclohexyl-1-phenyl-1-hydroperoxide in the cleavage reaction mixture and produce a cleavage effluent containing phenol and cyclohexanone, wherein the process is monitored by removing a sample of the cleavage reaction medium having sulfuric acid present comprising the steps;
(d) combining trimethylphosphine oxide (TMPO) with the sample to provide a series of mixtures having different $[H^+]/[TMPO]$ ratios of less than 1.0 and containing both TMPO and protonated TMPO;
(e) measuring the chemical shift of mixtures by $^{31}P$ NMR;
(f) plotting the chemical shifts against the $[H^+]/[TMPO]$ ratios to determine the slope of the linear fit;
(g) comparing the slope of the linear fit to that of a standardized sample comprising the same components of the reaction medium; and
(h) determining whether one or more components of the reaction medium should be adjusted to provide for maximum acid strength.

E30. The method of E29, wherein in step (e), the $^{31}P$ NMR chemical shift data is referenced against $H_3PO_4$.

The present disclosure will now be more particularly described with reference to the following non-limiting examples.

EXAMPLES

Figure 3:
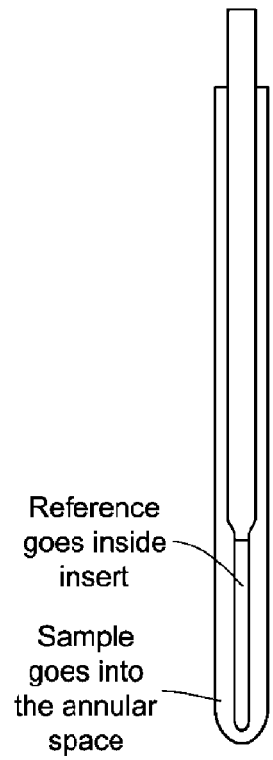
FIG. 3 depicts NMR tubes with a co-axial insert for $^{31}$P NMR measurements described herein.

In the examples, all ppm, parts and percentages and by weight unless otherwise indicated. The following abbreviations are used in the examples in other sections of the present disclosure:
CHB: cyclohexylbenzene
PhOH: phenol
CyONE: cyclohexanone
Method NMR tubes with a co-axial insert (Wilmad Glass, FIG. 3) were used for $^{31}P$ NMR measurements. A solution of 20% $H_3PO_4$ in $D_2O$ was loaded in the insert as the chemical shift reference (δ=0 ppm). The $D_2O$ also provides signal lock for NMR.

A 100 mM solution of TMPO was prepared by dissolving the desired amount of TMPO (Alfa Aesar) in the medium to be measured. A stock solution of $H_2SO_4$ (0-10 wt %) was prepared by dissolving concentrated $H_2SO_4$ (96%) in anhydrous 1,2-dimethoxyethane (glyme, 99.5%, Aldrich). An amount of 0.5 g of TMPO solution was charged to the NMR tube, 30 μL acid solution in glyme added, and the insert fitted. $^{31}P$ NMR (161.97 MHz, on a Bruker Biospin 400 MHz spectrometer) was measured immediately. The $[H^+]/[TMPO]$ mole ratio is varied by using different concentrations of $H_2SO_4$ solutions. $H_2SO_4$ was treated as a mono-acid. Thus, $[H^+]$ is the concentration of $H_2SO_4$ in mole·liter$^{-1}$; and [TMPO] is the concentration of TMPO added to the measurement medium in mole·liter$^{-1}$. The $H_2SO_4$ used in the examples herein are not intentionally enriched with deuterium or tritium isotopes. Thus, it is believed that the hydrons contained in this acid comprise protons, deuterons and tritons at percentages corresponding to their respective natural abundances.

Example 1

Measurement of $H_2SO_4$ Acid Strength in Water

An amount of 92.08 mg of TMPO was dissolved in 10 g of di-ionized (DI) water to prepare a 100 mM solution. 0.5 g of the solution was added to an NMR tube, and 30 μL glyme added. The insert containing 20% $H_3PO_4$ in $D_2O$ was fitted into the NMR tube and $^{31}$P NMR acquired. A single peak was observed at a chemical shift of 53.09 ppm (referenced to 20 wt % $H_3PO_4$ in $D_2O$).

Figure 4:
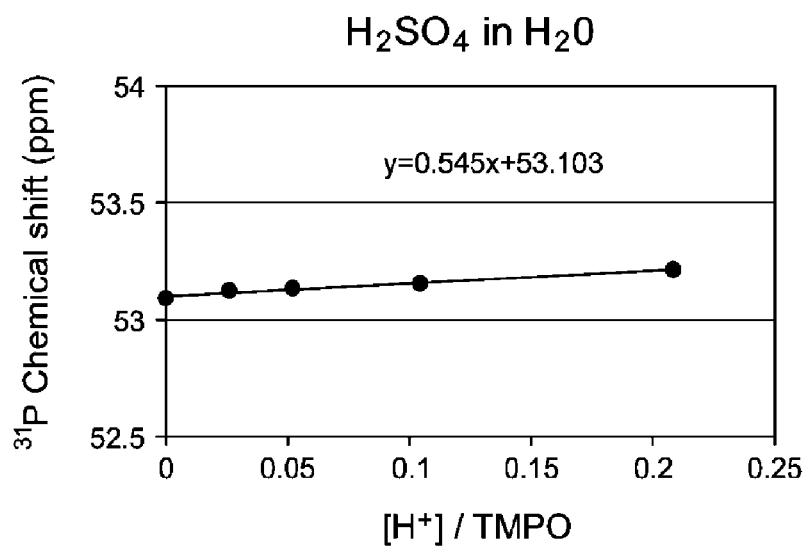
FIG. 4 depicts $^{31}$P NMR chemical shifts plotted against [H$^+$]/[TMPO] ratios in water. The slope of the linear fit line is 0.55, which is defined as the acid strength of H$_2$SO$_4$ in water. H$_2$SO$_4$ acid strength in water is independent on concentration (the non-zero slope supports this). H$_2$SO$_4$ in water is weaker than the same concentration in, for example, phenol/CyONE. This is consistent with experimental observations that cleavage of hydroperoxides in water is orders of magnitude slower than in PhOH/CyONE.

A series of stock solutions containing different concentrations of $H_2SO_4$ in glyme was prepared. $^{31}$P NMR was acquired in the same manner as above except 30 μL of $H_2SO_4$ solution in glyme was used. A single peak was observed in each case; and the chemical shifts were plotted against [H$^+$]/[TMPO] ratios (a ratio of 0.1 is equivalent to 1000 ppm of $H_2SO_4$). The slope of the linear fit line was 0.55, which is defined as the acid strength of $H_2SO_4$ in water (FIG. 4). [H$^+$]=[$H_2SO_4$]; the second dissociation is negligible: $K_1/K_2=10e^8$. [TMPO] is the concentration of TMPO added or used for the measurement (not the actual concentration as a result of the equilibrium)

Example 2

Measurement of $H_2SO_4$ Acid Strength in 80/20 (Weight Ratio) Cyclohexylbenzene (CHB)/Cyclohexanone (CyONE)

An amount of 92.08 mg of TMPO was dissolved in 10 g of 80/20 (weight ratio) CHB/CyONE to prepare a 100 mM solution. 0.5 g of the solution was added to an NMR tube, and 30 μL glyme added. The insert containing 20% $H_3PO_4$ in $D_2O$ was fitted into the NMR tube and $^{31}$P NMR acquired. A single peak was observed at 31.45 ppm.

Figure 5:
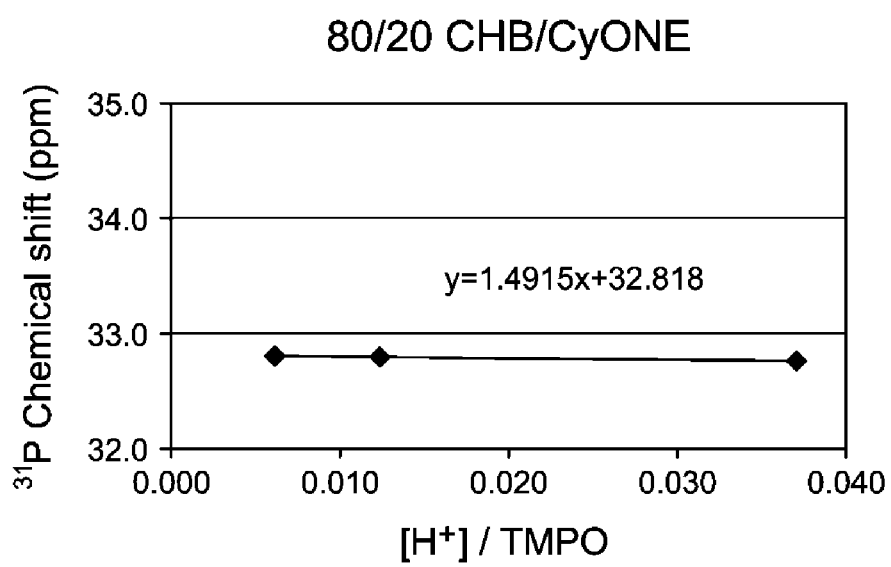
FIG. 5 depicts $^{31}$P NMR chemical shifts plotted against [H$^+$]/[TMPO] ratios in a mixture of cyclohexylbenzene (CHB) and cyclohexanone (CyONE). The slope of the linear fit line is −1.5, which is defined as the acid strength of H$_2$SO$_4$ in 80/20 (by weight) CHB/CyONE.

A series of stock solutions containing different concentrations of $H_2SO_4$ in glyme was prepared. $^{31}$P NMR was acquired in the same manner as above except 30 μL of $H_2SO_4$ solution in glyme was used. A single peak was observed in each case; and the chemical shifts were plotted against [H$^+$]/[TMPO] ratios (a ratio of 0.1 is equivalent to 1000 ppm of $H_2SO_4$). The slope of the linear fit line was −1.5, which is defined as the acid strength of $H_2SO_4$ in 80/20 CHB/CyONE (by weight) (FIG. 5).

Example 3

Measurement of $H_2SO_4$ Acid Strength in 80/20 (Weight Ratio) Cyclohexylbenzene (CHB)/Phenol (PhOH)

An amount of 92.08 mg of TMPO was dissolved in 10 g of 80/20 (weight ratio) CHB/PhOH to prepare a 100 mM solution. 0.5 g of the solution was added to an NMR tube, and 30 μL glyme added. The insert containing 20% $H_3PO_4$ in $D_2O$ was fitted into the NMR tube and $^{31}$P NMR acquired. A single peak was observed at 49.15 ppm.

Figure 6:
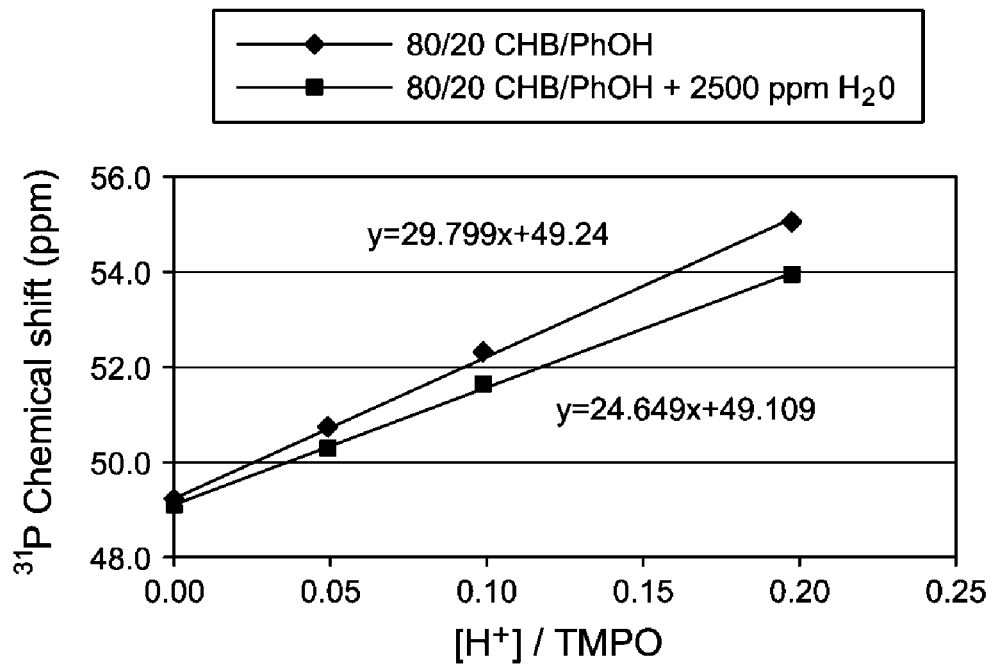
FIG. 6 depicts $^{31}$P NMR chemical shifts as a function of [H$^+$]/[TMPO] ratios in a mixture of cyclohexylbenzene (CHB)/phenol (PhOH). The slope of the linear fit line is 30, which is defined as the acid strength of H$_2$SO$_4$ in 80/20 (by weight) CHB/PhOH (diamond symbol). To measure the effect of water on the acid strength, 2500 ppm of de-ionized (DI) water was added to the 100 mM TMPO solution in CHB/PhOH before acid was added. With the addition of 2500 ppm H$_2$O, the acid strength decreases to 25 (square symbol).

A series of stock solutions containing different concentrations of $H_2SO_4$ in glyme was prepared. $^{31}$P NMR was acquired in the same manner as above except 30 μL of $H_2SO_4$ solution in glyme was used. A single peak was observed in each case; and the chemical shifts were plotted against [H$^+$]/[TMPO] ratios (a ratio of 0.1 is equivalent to 1000 ppm of $H_2SO_4$). The slope of the linear fit line was 30, which is defined as the acid strength of $H_2SO_4$ in 80/20 CHB/PhOH (FIG. 6, diamond symbol).

To measure the effect of water on the acid strength, 2500 ppm of DI water was added to the 100 mM TMPO solution in CHB/PhOH before acid was added. With the addition of 2500 ppm $H_2O$, the acid strength decreased to 25 (FIG. 6, square symbol).

Example 4

Measurement of $H_2SO_4$ Acid Strength in 80/10/10 (Weight Ratio) Cyclohexylbenzene (CHB)/Phenol (PhOH)/Cyclohexanone (CyONE)

An amount of 92.08 mg of TMPO was dissolved in 10 g of 80/10/10 (weight ratio) CHB/PhOH/CyONE to prepare a 100 mM solution. 0.5 g of the solution was added to an NMR tube, and 30 μL glyme added. The insert containing 20% $H_3PO_4$ in $D_2O$ was fitted into the NMR tube and $^{31}$P NMR acquired. A single peak was observed at 45.28 ppm.

Figure 7:
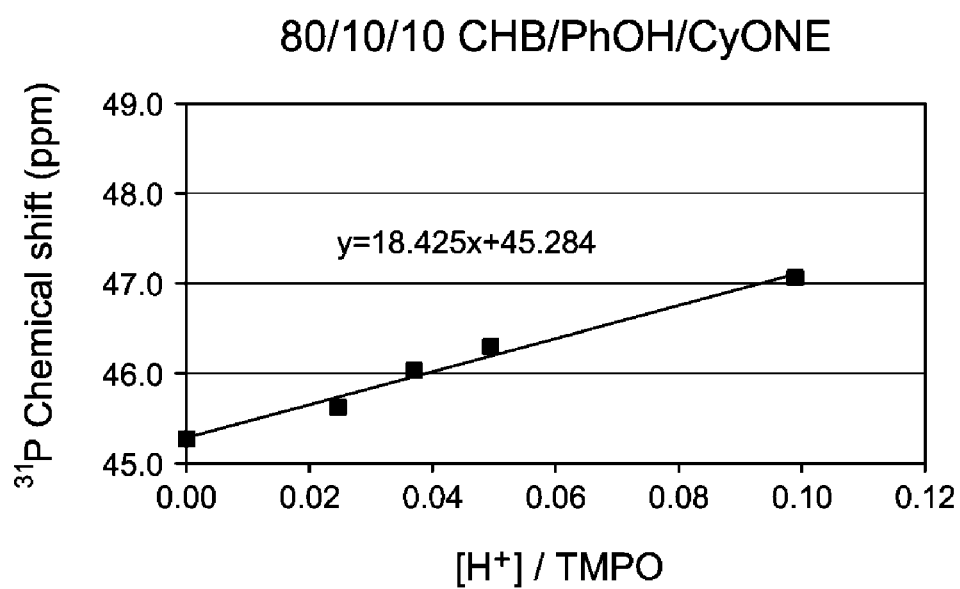
FIG. 7 depicts $^{31}$P NMR chemical shifts as a function of [H$^+$]/[TMPO] ratios in a mixture of cyclohexylbenzene (CHB)/phenol (PhOH)/cyclohexanone (CyONE) (80/10/10) by weight. The slope of the linear fit line is 18, which is defined as the acid strength of H$_2$SO$_4$ in 80/10/10 CHB/PhOH/CyONE.

A series of stock solutions containing different concentrations of $H_2SO_4$ in glyme was prepared. $^{31}$P NMR was acquired in the same manner as above except 30 μL of $H_2SO_4$ solution in glyme was used. A single peak was observed in each case; and the chemical shifts are plotted against [H$^+$]/[TMPO] ratio (a ratio of 0.1 is equivalent to 1000 ppm of $H_2SO_4$). The slope of the linear fit line was 18, which is defined as the acid strength of $H_2SO_4$ in 80/10/10 CHB/PhOH/CyONE (by weight) (FIG. 7).

Acid strength of $H_2SO_4$ in various liquid media was measured using the method described herein and the results are summarized in Table 1.

TABLE 1

| Media Sample No. | Composition | | | | | Acid Strength |
|---|---|---|---|---|---|---|
| | CHB (wt %) | PhOH (wt %) | CyONE (wt %) | $H_2O$ (ppm wt) | $H_2O$ (wt %) | |
| 1 | 40 | 30 | 30 | 5000 | — | 28 |
| 2 | 40 | 30 | 30 | 0 | — | 32 |
| 3 | 51 | 30 | 19 | 1700 | — | 21 |
| 4 | 51 | 30 | 19 | 0 | — | 32 |
| 5 | 80 | 20 | 0 | 0 | — | 30 |
| 6 | 80 | 20 | 0 | 2500 | — | 25 |
| 7 | 80 | 20 | 0 | 5000 | — | 12 |
| 8 | 80 | 10 | 10 | 0 | — | 18 |
| 9 | 80 | 0 | 20 | 0 | — | −1.5 |
| 10 | 0 | 0 | 0 | — | 100 | 0.5 |

In summary, a quantitative method to measure the acid strength of $H_2SO_4$ in various liquid media is established. Using $H_2SO_4$ in water as a standard, a quantitative acid strength scale is established, as shown in the table. The method is fast, easy to use, and sensitive to the nature of the liquid medium.

The invention claimed is:

1. A method to determine the strength of an acid in a medium comprising:
   (I) providing multiple samples comprising trimethylphosphine oxide (TMPO), the acid, and the medium, the multiple samples having different [H$^+$]/[TMPO] ratios of less than 1.0, where [H$^+$] is the concentration of hydrons in the sample in mole·liter$^{-1}$, and [TMPO] is the concentration of TMPO used in the sample in mole·liter$^{-1}$; and
   (II) measuring the $^{31}$P chemical shifts of the multiple samples by $^{31}$P NMR.

2. The method of claim 1, further comprising:
   (III) determining the acid strength in the medium by plotting the $^{31}$P chemical shift (ppm) versus the [H$^+$]/[TMPO] ratio.

3. The method of claim 2, wherein the step (III) of determining the acid strength comprises:
   (IIIa) drawing $^{31}$P chemical shift versus [H$^+$]/[TMPO] data points in a coordinate system;

(IIIb) providing a linear fitting of the data points; and
(IIIc) determining the slope of the linear fitting.

4. The method of claim 1, wherein the medium comprises at least one of (i) a solvent, (ii) a reactant, (iii) water, and (iv) a product of a reaction system.

5. The method of claim 4, wherein the reaction system includes a chemical reaction dependent on the acid strength of the acid.

6. The method of claim 4, wherein the reaction system includes a cleavage reaction of a hydroperoxide compound.

7. The method of claim 6, wherein the medium comprises cyclohexylbenzene, cyclohexanone, phenol, water or combinations of two or three thereof.

8. The method of claim 6, wherein the medium comprises cumene, acetone, phenol, water, or combinations of two or three thereof.

9. The method of claim 1, wherein the acid is sulfuric acid.

10. The method of claim 1, wherein the medium has:
a cyclohexylbenzene concentration in a range from 5 wt % to 90 wt %;
a phenol concentration in a range from 0 wt % to 90 wt %;
a cyclohexanone concentration in a range from 0 wt % to 90 wt %; and
a water concentration in a range from 0 ppm to 1 wt % (10000 ppm by weight);
where all concentrations are based on the total weight of the medium.

11. The method of claim 10, wherein the strength of the acid varies from −10 to 60.

12. A method for optimizing reaction conditions of a reaction system, the method comprising:
(A) providing a sample comprising a reaction medium and an acid;
(B) combining trimethylphosphine oxide (TMPO) with aliquots of the sample to provide a series of mixtures containing both TMPO and protonated TMPO and having different [H$^+$]/[TMPO] ratios of less than 1.0;
(C) measuring the chemical shifts of the mixtures by $^{31}$P NMR;
(D) plotting the chemical shifts against the [H$^+$]/[TMPO] ratios to determine the slope of a linear fit;
(E) comparing the slope of the linear fit to that of a standardized sample comprising the same components of the reaction medium; and
(F) determining whether one or more components of the reaction medium and/or amount thereof should be adjusted to provide for a desired acid strength.

13. The method of claim 12, wherein the reaction system includes a chemical reaction dependent on the acid strength of the acid.

14. The method of claim 12, wherein the reaction system includes a cleavage reaction of a hydroperoxide compound.

15. The method of claim 14, wherein the reaction medium comprises cyclohexylbenzene, cyclohexanone, phenol, water, or combinations of two or three thereof.

16. The method of claim 12, wherein the reaction medium comprises cumene, acetone, phenol, water or combinations of two or three thereof.

17. The method of claim 12, wherein the acid is sulfuric acid.

18. The method of claim 12, wherein the medium has:
a cyclohexylbenzene concentration in a range from 5 wt % to 90 wt %;
a phenol concentration in a range from 0 wt % to 90 wt %;
a cyclohexanone concentration in a range from 0 wt % to 90 wt %; and
a water concentration in a range from 0 ppm to 1 wt % (10000 ppm) by weight;
where all concentrations are based on the total weight of the medium.

19. The method of claim 18, wherein the strength of the acid varies from −10 to 60.

20. A method for monitoring a process for producing phenol and cyclohexanone, the process comprising:
(a) providing a cleavage feed containing greater than 10 wt % and no greater than 95 wt % cyclohexyl-1-phenyl-1-hydroperoxide, and at least 5 wt % and less than 90 wt % cyclohexylbenzene;
(b) mixing the cleavage feed with at least phenol, cyclohexanone, water, and sulfuric acid, to produce a cleavage reaction mixture containing from 10 wt % to 80 wt % phenol, from 10 wt % to 60 wt % cyclohexanone, from 0.5 wt % to 10 wt % cyclohexyl-1-phenyl-1-hydroperoxide, from 3 wt % to 60 wt % cyclohexylbenzene, from 0.01 wt % to 4 wt % water, and from 10 ppm to 1000 ppm sulfuric acid, where all concentrations are based on the total weight of the cleavage reaction mixture; and
(c) reacting the cleavage reaction mixture at a temperature from 20° C. and to 90° C. for a time sufficient to convert at least 50% of the cyclohexyl-1-phenyl-1-hydroperoxide in the cleavage reaction mixture and produce a cleavage effluent containing phenol and cyclohexanone;
wherein the process is monitored by:
(m1) taking a sample of the cleavage reaction mixture;
(m2) combining trimethylphosphine oxide (TMPO) with a series of aliquots of the sample to provide a series of mixtures containing both TMPO and protonated TMPO and having different [H$^+$]/[TMPO] ratios of less than 1.0;
(m3) measuring the chemical shifts of the mixtures by $^{31}$P NMR;
(m4) plotting the chemical shifts against the [H$^+$]/[TMPO] ratios to determine the slope of the linear fit;
(m5) comparing the slope of the linear fit to that of a standardized sample comprising the same components of the reaction medium; and
(m6) determining whether one or more components of the cleavage mixture and/or amount thereof should be adjusted to provide for a desired acid strength.

21. The method of claim 20, wherein the step (m4) of determining the linear fit comprises:
(m4a) drawing $^{31}$P chemical shift versus [H$^+$]/[TMPO] data points in a coordinate system;
(m4b) providing a linear fitting of the data points; and
(m4c) determining the slope of the linear fitting.

* * * * *